United States Patent [19]

Boyer

[11] Patent Number: 5,295,200
[45] Date of Patent: Mar. 15, 1994

[54] METHOD AND APPARATUS FOR DETERMINING THE ALIGNMENT OF AN OBJECT

[75] Inventor: Arthur L. Boyer, Houston, Tex.

[73] Assignee: Board of Regents, The University of Texas System, Austin, Tex.

[21] Appl. No.: 985,367

[22] Filed: Dec. 3, 1992

Related U.S. Application Data

[63] Continuation of Ser. No. 638,895, Jan. 9, 1991, abandoned.

[51] Int. Cl.$^5$ .............................................. G06K 9/32
[52] U.S. Cl. .......................................... 382/43; 382/6; 382/45
[58] Field of Search .................... 382/6, 42, 43, 44, 45

[56] References Cited

U.S. PATENT DOCUMENTS

| | | | |
|---|---|---|---|
| 3,777,124 | 12/1973 | Povkovich | 235/151 |
| 3,783,251 | 1/1974 | Pavkovich | 235/151 |
| 4,118,631 | 10/1978 | Froggatt | 250/792 R |
| 4,247,780 | 1/1981 | Webber et al. | 250/491 |
| 4,365,341 | 12/1982 | Lam | 378/65 |
| 4,547,800 | 10/1985 | Masaki | 358/107 |
| 4,558,462 | 12/1985 | Horiba et al. | 382/42 |
| 4,633,494 | 12/1986 | Klausz | 378/205 |
| 4,764,944 | 8/1988 | Finlayson | 378/20 |
| 4,791,934 | 12/1988 | Brunnett | 128/653 |
| 4,843,631 | 6/1989 | Steinpichler et al. | 382/43 |
| 4,895,431 | 1/1990 | Tsujiuchi et al. | 350/320 |
| 5,020,111 | 5/1991 | Weber | 382/31 |

OTHER PUBLICATIONS

Mok et al., "Encoding patient contours using Fourier descriptors for computer treatment planning", *Med. Phys.*, 13(3):413–415, May/Jun. 1986.

Lam et al., "An on-line electronic portal imaging system for external beam radiotherapy", *The British Journal of Radiology*, 59:1007–1013, 1986.

Perry et al., "Medical Image Reconstruction: Multiangular Sectional Roentgenography by Computer", High Altitude Observatory, National Center for Atmospheric Research, Boulder, Colo., Aug. 1975.

Nishikawa et al., "Signal-to-noise properties of mammographic film-screen systems", *Med. Phys.*, 12(1):32–39, Jan./Feb. 1985.

Kelsey et al., "Measurement of Patient Movement During Radiation Therapy", *Radiology*, 103:697–698, Jun. 1972.

*Primary Examiner*—David K. Moore
*Assistant Examiner*—Andrew W. Johns
*Attorney, Agent, or Firm*—Arnold, White & Durkee

[57] ABSTRACT

A method and apparatus are provided for quickly determining misalignment between two images. Patient misalignment calculations can performed on-line using Fourier correlation analysis to compare the location of a portal field of radiation with a previously stored portal reference field. Fourier comparisons are done in both hardware and software which rapidly computes misalignment of a patient relative to the portal field and can also rapidly reposition the patient with respect to that field.

7 Claims, 2 Drawing Sheets

METHOD AND APPARATUS FOR DETERMINING THE ALIGNMENT OF AN OBJECT

The government has certain rights in the invention.

This is a continuation of application Ser. No. 07/638,895, filed Jan. 9, 1991.

Incorporated herein is a computer program listing printout appendix of source code used to verify the alignment of images such as radiotherapy images used in radiotherapy treatment systems of the present invention. Copyright 1989 The University of Texas, M. D. Anderson Cancer Center.

A portion of the disclosure of this patent document contains material which is subject to copyright protection. The copyright owner has no objection to the facsimile to production by any one of the patent documents or the patent disclosure, as it appears in the Patent and Trademark Office, patent files or records, but otherwise reserves all copyright rights whatsoever.

BACKGROUND OF THE INVENTION

This invention relates to a means of measuring the degree of similarity between two images. Specifically, it relates to a method of aligning and verifying the alignment of images such as radiotherapy images used in radiotherapy treatment systems. More specifically, the present invention is directed toward an improved method and apparatus for processing and comparing a reference image to one or more portal fields of radiation using Fourier correlation techniques.

Radiotherapy treatment is generally used to supply dosages of radiation upon isolated portions of a patient's body. Dosages of radiation are often used in the treatment of cancer. However, when supplying radiation upon a patient's body, it is crucial that the cancerous portion be isolated, and radiation be supplied only toward that portion. With modern radiotherapy equipment, carefully collimated radiation beams (called treatment portals) can irradiate localized cancerous tissue while sparing much of the surrounding normal tissue. Conventional radiotherapy consists of about 30 consecutive daily treatments using one or two portals each day. Repositioning of the patient is critically important for success of therapy. Therefore, it is important that during each radiation treatment session, the treatment portals be aligned consistently upon the cancerous tissue. By fixing the radiation portals upon a specific portion of the patient's body during each treatment session, the radiotherapist is ensured that maximum effective treatment of the patient's cancerous tissue will be maintained while minimizing radiation exposure to normal tissue.

Conventional alignment systems use pre-therapy portal filming to verify and maintain the proper alignment and position of a portal. Verification using pre-therapy filming is severely limited by the time required to develop the film and the logistics of film evaluation and storage. Pre-therapy filming entails too great a time delay between exposure of the film and review of the developed image to allow image evaluation before irradiation of the patient. Current practice is to delay review of the portal film until after the filmed therapy session and before the next therapy session. The time and expense required to acquire an image on conventional x-ray film also precludes daily evaluation of portal alignment. In an effort to overcome these problems, recent advances in the technology of high resolution detection of energetic radiation have made practical on-line electronic portal imaging devices (EPIDs). EPIDs make it possible to record and evaluate images on-line and prior to the delivery of each radiation dose. On-line monitoring allows a patient to be repositioned in accordance with the radiation portal and during radiation treatment.

Using EPIDs, one may test the sequence of images, $f_{test}$, acquired during a course of therapy against a standard image, $f_{ref}$. A reference image is identified which outlines a fairly precise location for which radiation treatments are desired. The reference image may be taken on-line with the EPID at the beginning of the treatment process, and the resulting reference image stored for subsequent use and comparison with portal images during future radiation treatment sessions. Alternatively, the reference image may be a digitally reconstructed radiograph computed from a serial sequence of CT scans of the patient or else it may also be derived from a simulation radiograph. The major problem with EPIDs is that comparison of reference images with subsequent radiation treatment portals is time consuming and requires the presence of the radiotherapist and/or communication of detailed acceptance criteria to trained technologists. Images conventionally consist of approximately $512 \times 512$ arrays of pixels of which each pixel can have a plurality of eight or twelve bits to encode gray levels. Thus it is possible to compare images numerically. However, it is difficult to ascertain what algorithm should be used for the comparison. Observation of the subtraction image, $f_{test} - f_{ref}$, provides a qualitative means of assessing portal alignment. But subtraction images provide no universal quantitative scale for measuring a degree of verification. Automated identification of specific and anatomical structures is not presently feasible with minicomputers. Another method is to superpose a graticule or scale generated by the computer over the image. Although quantitative assessment may be made of identifiable features which intersect the scale, this method still gives no global measure of the degree of similarity between two images.

SUMMARY OF THE INVENTION

Accordingly, it is desirable to provide a method and apparatus which can rapidly and efficiently process image portals and compare one or more image portals to previously stored reference portals. The present invention concerns an improved technique by which images can be quickly processed and compared. One method entails Fourier correlation analysis. Correlation analysis between two images provides a universal scale on which one can measure a degree of object alignment. With such a scale, one can set alignment tolerances that are considered to be acceptable. Correlation analysis of the object detected in the images can be used to measure the degree of correctness of the position of the object with respect to the portal image. It is understood that the present alignment verification system of the present invention is operable to quickly verify the alignment of any object which includes but is not limited to anatomical objects (i.e, a patient, etc.)

Broadly speaking, the present invention is a method and apparatus for processing images quickly and efficiently using an algorithm that is sensitive to global similarities between two images. Furthermore, the present algorithm can be achieved using standard hardware and can be processed using conventional micro computers purchased over the counter. If a patient's radiation portal should be misaligned with respect to the reference portal, the patient and/or radiation portal can be repositioned to provide precise treatment of only the cancerous tissue within the patient's body. Because the present invention allows a universal scale to be used to measure portal alignment, it is feasible for a physician to prescribe simply and objectively the degree of alignment to be achieved to the technologist carrying out the treatment procedure.

Accordingly, the present invention provides a method for quantifying the similarity between two images using a portal field of view positioned with respect to an object. The portal field of view may include carefully collimated imaging rays or x-ray and radiation portal beams which are directed to irradiate cancerous tissue while sparing much of the surrounding normal tissue. A portal image, $f_{i,j}$, is created from the portal field of radiation, where f is the pixel value in the range $0 \leq f \leq 255$ for an eight bit image; i is the pixel index in the range from 1 to a maximum (possibly, i=512) and j is the orthogonal pixel index in the range from 1 to a maximum (possibly, j=512). Next, a correlation array is generated by processing and fast Fourier transformation (FFT) of each of the portal images. Each of image arrays are correlated with a previously stored reference array to determine an alignment difference between anatomy revealed in each of the image arrays and visible in the reference array. Depending upon values within the correlation array, the patient can be repositioned such that radiation treatment can be refocused upon the cancerous tissue defined by the reference image. Once the portal image is realigned, radiation treatments are then directed toward the proper location on the patient. The reference array is generated and stored prior to creating the portal image. Reference portal images may be created similar to the portal images by collimated radiation beams traversing a patient during radiation treatment therapy. Reference portal images are stored for subsequent use as guideposts or landmarks for directing portal treatment images during subsequent treatment sessions.

Specifically, the step of comparing with Fourier correlation analysis each of the image arrays with the previously stored reference array comprises mathematically comparing the loci of isocorrelation curves of selected values (in particular, the maximum value) with isocorrelation curves of the same values in the autocorrelation of the reference image. This objective is universally applicable, and can be computer automated.

In accordance with the instant invention, there is also provided a novel method for obtaining rapid numerical measure of the difference in position between the portal image traversing a patient and the previously stored reference image. The location of the correlation array maximum is directly related to translations of the patient in directions normal to the axis of rotation of the treatment machine collimator.

In accordance with the instant invention, there is also provided a novel apparatus for on-line alignment and treatment of patients with radiation. The apparatus comprises an electronic portal imaging device (EPID) associated with a radiotherapy apparatus for emitting collimated radiation. A detector is positioned within the path of travel of the emitted radiation to receive the radiation after having been passed through the patient. The detector has means for converting the received radiation to light and to record the light, and various contrasts of the light, in the form of a portal image. Thus, each portal displays a focused image or portal window of a portion of the patient's body. The portal image can be digitized into binary bit strings corresponding to an image array of pixels, each pixel having a plurality of gray levels showing contrast within the image array of bone or tissue traversed by the radiation field. A memory device is coupled to the digitizer to store one or more selective binary bits streams corresponding to the reference and portal arrays for later recall during the comparison routine. An array processor, connected to the output of the digitizing means is used for correlating and comparing the image array with the reference array. The processor is a fast and efficient means of obtaining the Fourier components of each array. In accordance with the resulting comparison value, the patient is repositioned with respect to the radiation portal in response to output from the array processor. Converting means further comprises a scintillating or fluorescent material coated on a plate to emit light when activated by radiation, and a video camera and computer coupled to the scintillator to digitize, display and store each portal image. It is understood that EPID includes a radiation generating means for defining selectively positioned radiation which can be shifted in space relative to the patient in response to output from the array processor.

Important features of this invention have thus been summarized rather broadly in order that the detailed description thereof that follows may be better understood, and in order that the contribution to the art may be better appreciated. There are, of course, additional features of the invention which will be described hereinafter in more detail and which will also form the subject of the claims appended hereto.

DETAILED DESCRIPTION OF PREFERRED EMBODIMENTS

Figure 1:
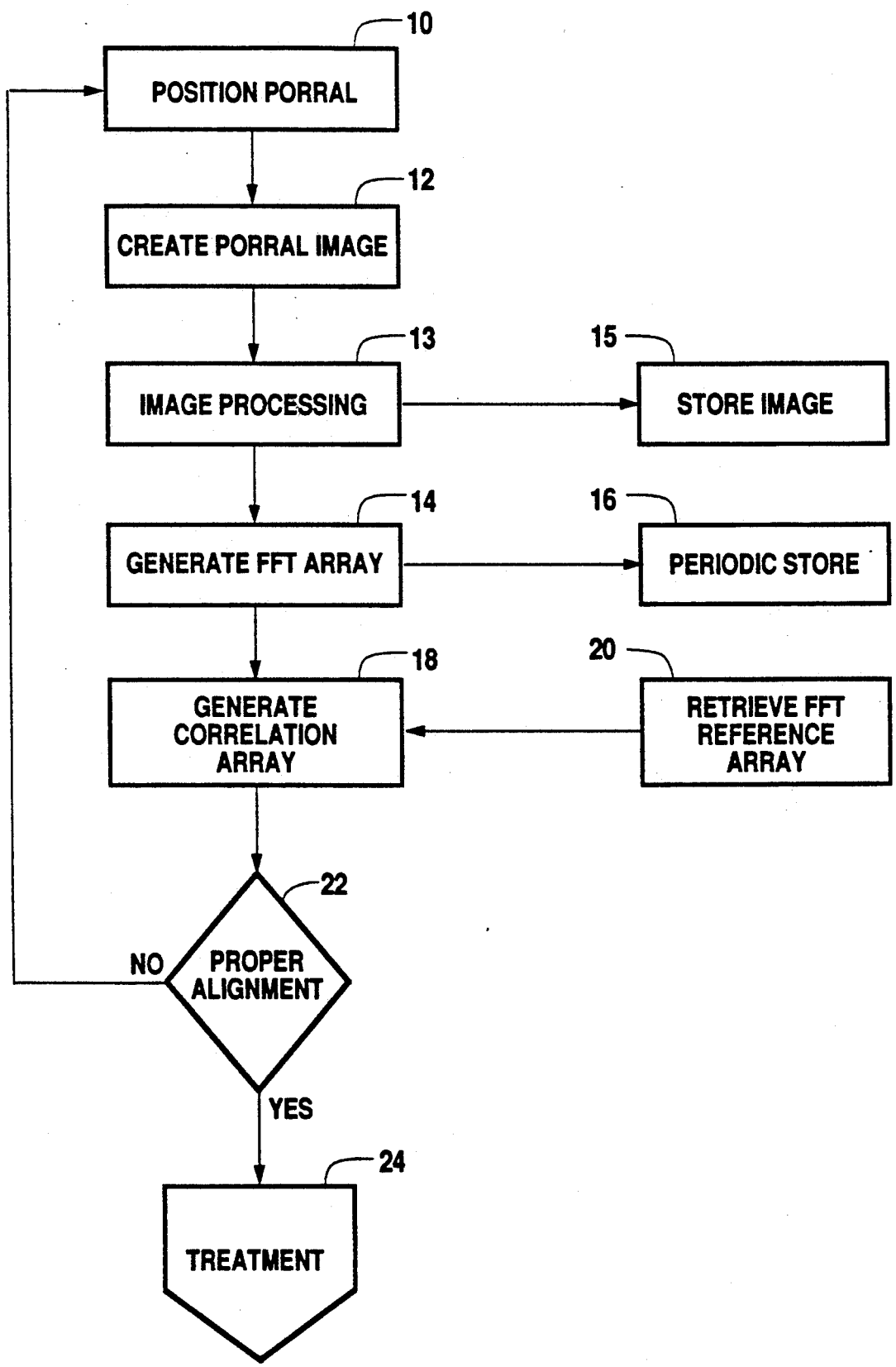
FIG. 1 is a flow diagram illustrating operation of the invention.

Referring to the drawings, FIG. 1 illustrates a flow diagram used in aligning objects in an industrial setting or for treating patients with radiation. Initially, an object or patient is positioned with respect to a portal field of radiation as indicated in block 10. If a patient is used, the patient is positioned and a portal image is created in block 12 corresponding to the portal field traversing the patient. The portal image corresponds to the bone, air, and tissue contrasts shown within the confines of the portal field. Next, the image is processed 13 into digital gray scales. The original image may be stored as in block 15. An FFT image array is generated by Fourier transforming each portal image as shown in block 14. Selective FFT arrays can be stored as shown in block 16 for future reference.

Block 18 describes an FFT correlation operation, which compares the FFT array in block 14 with an FFT reference array of block 20 retrieved from local memory. The FFT reference array corresponds to a previously stored array having the desired boundary location of one portal field of radiation with respect to cancerous tissue. Block 18 is used to generate the correlation array in the frequency domain using the FFTs of the reference array and the portal image array. As shown in decision block 22, if the portal image array is misaligned from the reference array, then radiation treatment is not carried out and the patient and/or portal field of radiation must be realigned or repositioned before treatment is executed. If, however, alignment is proper, then treatment will be executed as shown in block 24.

FFT correlations, shown in block 18, use the technique of Fourier correlation analysis. Fourier correlation analysis provides a universal scale on which one can measure a degree of patient alignment with a benchmark reference point (reference array). With such a universal scale, one can set alignment tolerances that are considered to be acceptable. Furthermore, Fourier correlation techniques are not only directly and immediately applicable to conventional radiotherapy, but they also have important applications for the development of conformal therapy. Conformal therapy is applied to a broad range of treatment techniques whose goal is to treat malignant tissue with as high a dose as possible by optimizing the shapes and directions of the irradiation fields. Conformal therapy techniques commonly employ computer controlled irradiation machines equipped with multileaf collimators. The dose delivered by each daily treatment is accumulated from many portals directed at the tumor from many angles. The multileaf collimator is used to provide an optimal field shape from each angle so as to cause the dose distribution to conform closely to the target volume. Dose and collimator settings are drawn from computer files. The system is complex and requires preventive checks on its operation. The present invention can be used to provide independent checks during conformal therapy treatment, thereby providing automated analysis techniques during the therapy treatment process.

Figure 2:
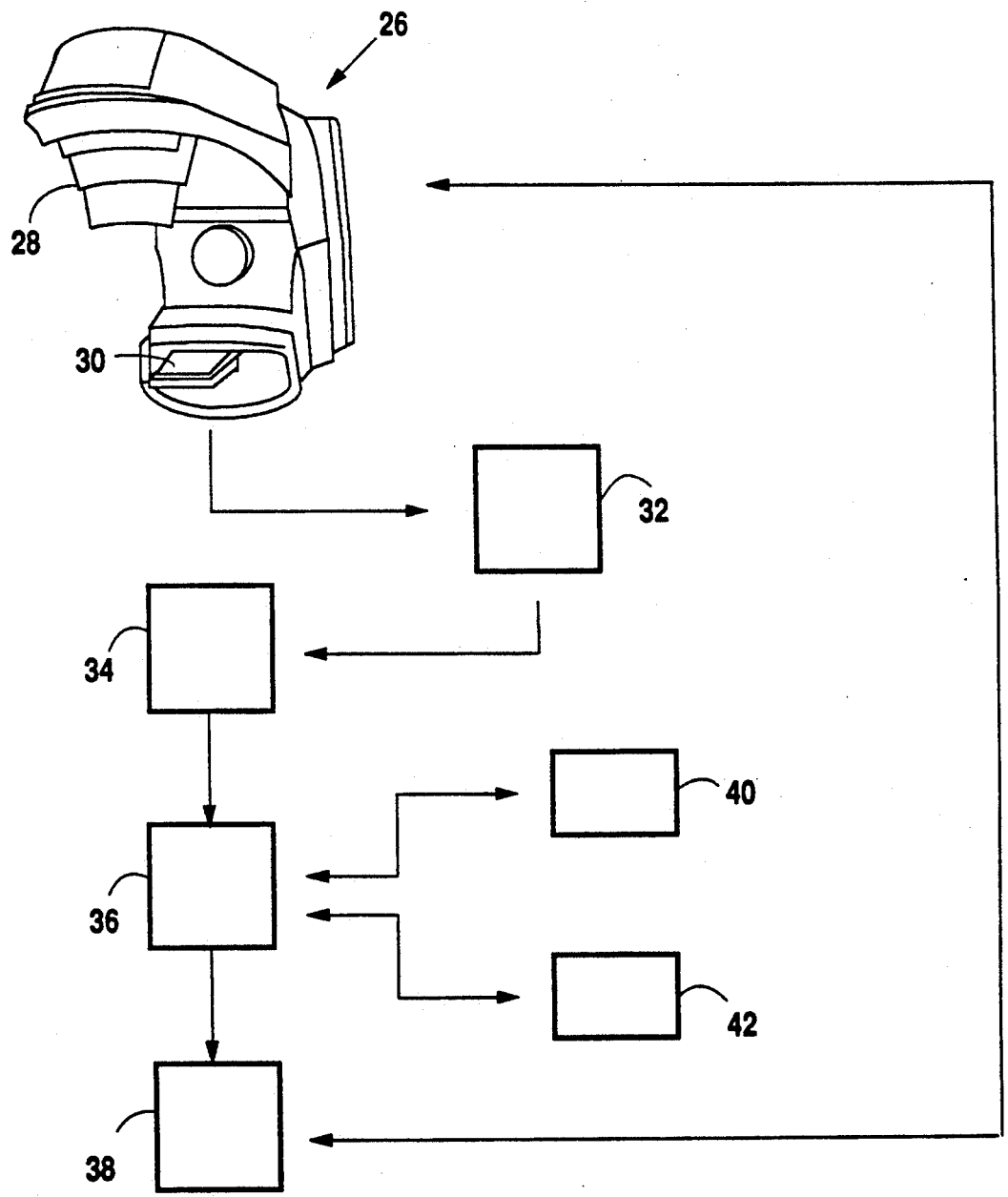
FIG. 2 is a block diagram illustrating the apparatus for aligning and treating patients with radiation according to the present invention.

The entire process shown in FIG. 1, can be done on-line using conventional hardware shown in FIG. 2. A linear accelerator 26 is used to emit collimated radiation upon a patient placed between a conventional or multileaf collimator 28 and an EPID 30. The patient is placed within the path of travel of the field of radiation such that a specific, localized area within the patient receives radiation treatment. Localization may be achieved by an EPID presently manufactured by Fiber Imaging, Inc. of St. Louis, Missouri. Such devices are capable of forming clear images from patient doses in the range of 0.25 cGy to 10 cGy with a resolution approaching 0.3 line pair/mm. It is important to note, however, that the EPIDs, collimators and/or accelerators specified herein are used only as examples, and that other forms may be used without departing from the scope of the invention.

The video output of the camera component 32 of the EPID 30 is captured by a digitizer or frame grabber 34 generally configured within or in association with a computer or microcomputer 36. Microcomputers having such a grabber mechanism may include a PC-AT clone with four Mbytes of RAM, a 150 Mbytes hard disk, a 40 Mbyte tape drive, and a super VGA monitor. However, it is to be appreciated that other types of microcomputers with varying hardware capabilities can be substituted and still adequately store and capture output from the camera 32 or its equivalent.

An optical digitizing system can be interfaced to the system to provide means for entering radiographic simulation films. These film can be compared with the EPID images of the first treatment to determine whether or not the simulation films can be used as a reference against which subsequent images can be compared.

After a portal image is produced and digitized, it is then converted to a two-dimensional FFT array. This may be facilitated by employing an array processor 40. The primary function of array processor 40 is to reduce the computation time required to form the FFT of the portal image and to carry out the array multiplication and divisions and inverse FFT that are needed to obtain a normalized correlation array. Thus, array processor 40 facilitates a clinical scoring technique for portal images. A useful scoring system must allow a threshold criteria to be established to distinguish an unacceptable level of patient/position verification from an acceptable level. The scoring system of the present invention is insensitive to size and degree of complexity of the image. Moreover, the present scoring system uses array processor 40 to carry out multidimensional Fourier transformations and image correlation using Fourier transformations in correlation integrals. Fourier correlation integrals are useful for obtaining a rapid numerical measure of the similarity between the portal image and the designated reference image. The correlation integral used in the present invention is as follows:

$$C(x,y) = \frac{\int\int f(x',y')g(x+x',y+y')dx'dy'}{\sqrt{\int\int f^2(x',y')dx'dy' \int g(x',y')g(x-x',y-y')dx'dy'}}$$

These integrals are evaluated in the frequency domain using the Fourier transforms:

$$C(x,y) = FFT\{c(x,y)\}$$

$$F(x,y) = FFT\{f(x,y)\}$$

$$G(x,y) = FFT\{g(x,y)\}$$

Using array processor 40, each Fourier transformation can be carried forth in approximately 1.5 seconds. Furthermore, each correlation is computed in the frequency domain, involving rapid multiplication according to the following equation:

$$C_{ij} = [I \cdot J]^{\frac{1}{2}} \frac{\mathcal{F}^{-1}\{F_{ij} \cdot G_{ij}^*\}}{\left[\sum_{i,j} |f_{i,j}|^2\right]^{\frac{1}{2}} [\mathcal{F}^{-1}\{G_{ij} \cdot G_{ij}^*\}]^{\frac{1}{2}}}$$

Thus, the correlation distribution C(x,y) can be obtained in a short period of time. The maximum value of the correlation can be compared to the maximum value of the auto correlation of the reference image to compare the degree of similarity between these two images.

Each of these computations can be carried forth using a Dell Model 310 computer employing a graphics terminal with software to display images. Software subroutines are used to subtract images, perform masking, convolution, Fourier transformation, take root-mean-square differences and calculate gradients. The correlation integral C(x,y) is indicative of the translational or rotational misalignment of the image portal relative to the reference portal.

In addition to determining the correlation integral C(x,y), the present invention can test for rotation of the patient about the axis of the treatment beam portal. Rotation can alternatively be determined based on the center of gravity (or first moment) of the portal image and is given by the vector whose components are:

$$<x> = \int_x \int_y x f(x,y) dx dy$$

$$<y> = \int_x \int_y y f(x,y) dx dy$$

These components can be evaluated in the frequency domain variable $f, \eta$ and computed from the Fourier transforms, $F(f, \eta)$, using the following equations:

$$<x> = \frac{\frac{2F}{2\zeta}(0,0)}{2\pi i F(0,0)}$$

$$<y> = \frac{\frac{2F}{2\eta}(0,0)}{2\pi \iota F(0,0)}$$

Rotation in the center of gravity vector indicates a rotation in the patient. If the magnitude of the vector is unchanged between the reference image and the portal image, then the patient has undergone a pure rotation.

In each case where the correlation integral, or rotation indicates patient misalignment, movement, rotation or radiation overexposure, the image portal and/or patient can be moved or repositioned by a repositioning device such as, e.g. a motor 38.

The foregoing description of the invention has been directed to particular embodiments, which not only maximize radiation to cancerous tissue while minimizing radiation to surrounding normal tissue, but also, performs comparison calculations, such as correlation, gradient, and rotation, to enable rapid repositioning of the patient in order to maximize radiation treatment effectiveness. While the invention has been described in what is presently conceived to be the most practical and preferred embodiment thereof, it will be apparent, however, to those skilled in the art that modifications and changes in both apparatus and method may be made without departing from the scope and spirit of the invention. For example, any form of hardware or software which performs substantial portions of this invention fall within the scope and spirit of the invention. Thus, the scope of this invention is to be accorded the broadest interpretation in accordance with the following claims so as to encompass all equivalent methods and devices, modifications and variations which fall within the true scope and spirit of this invention.

The above calculations laid forth in the microprocessor 36 and/or the array processor 40 are all performed in software code to provide each of the following functions: 1) Analysis of the degree of translation and rotation of patient anatomy by application of Fourier correlation functions analysis, image substraction, visual comparison against fiducial marks and other techniques; 2) Analysis of field margin reproducability by correlation and moment calculation; 3) Correlation of high energy megavoltage x-ray images with diagnostic quality kilavoltage x-ray images; and 4) Computer generation of synthetic images by ray-tracing through CT data including, but not limited to, calculations of the correlation integral, gradients, and/or patient rotation, all performed in software code as shown in the following source code listings, Copyright 1990, The University of Texas System:

What is claimed is:

1. A method for quantifying the similarity between two images, comprising:

providing a portal field of view;

positioning a portion of an object within said portal field of view;

radiating said object to create a portal image corresponding to said portal field of view with respect to said object;

generating an FFT array of the image by fast Fourier transforming said portal image;

performing a Fourier correlation of said FFT array with a previously stored reference array to yield a correlation array;

preparing an inverse FFT of said correlation array;

calculating a universal scale as a function of said inverse FFT;

setting alignment tolerances using said universal scale;

comparing said alignment tolerances with the normalized Fourier correlation of each said array with a previously stored reference array to determine an alignment criteria between each said image array and said reference array; and repositioning said object with respect to said portal image if said alignment criteria exceeds said alignment tolerances.

2. The method as recited in claim 1, further comprising:

providing a reference portal field of view upon the portion of a patient corresponding to a location desiring radiation treatment;

creating a reference portal image corresponding to said reference portal field of view with respect to a patient;

generating an FFT reference array by fast Fourier transforming each said reference portal image;

storing said reference array for subsequent use in Fourier analysis;

comparing said portal image with said reference portal image by a normalized correlation integral implemented with fast Fourier transforms to determine measure of alignment;

repositioning a patient with respect to said portal field if said measure of alignment exceeds an acceptable margin; and continuing radiation treatment of said portal field upon the proper location on said patient.

3. The method as recited in claim 1, wherein said comparing step further comprises:

generating a reference portal image;

generating said reference image into an FFT reference array by Fourier transforming each said reference image into a reference array;

storing each said reference array; and comparing each said reference array with subsequently generated said FFT array for each said portal field of radiation.

4. An apparatus for on-line alignment and treatment of a patient with radiation, comprising:

means for emitting collimated radiation;

a detector aligned to receive said collimated radiation after having passed through said patient, and to produce signals indicative of said received radiation;

means for storing said signals in the form of a portal image;

means for Fourier converting said portal image into an FFT image array;

a memory device coupled to said Fourier converting means and adapted to stored a Fourier converted reference array;

an array processor means connected to the output of said Fourier converting means for correlating said FFT image array and said reference array to produce a correlation array, for calculating an inverse FFT of said correlation array, for calculating a universal scale as a function of said inverse FFT to measure a degree of patient alignment, and for comparing alignment criteria with predetermined alignment tolerances on the universal scale; and means for repositioning said patient with respect to said radiation portal in response to input from said array processor.

5. The apparatus as recited in claim 4, wherein said converting means further comprises:
   a scintillator material coated on a copper plate to emit light when activated by radiation; and
   a video camera and microcomputer coupled to said scintillator to display and store each said portal image.

6. The apparatus as recited in claim 4, wherein said emitting means comprises a multileaf accelerator which directs selectively positioned radiation relative to said patient.

7. The apparatus as recited in claim 4, wherein said detector having spatial and temporal resolution capable of detecting portal images of selective regions of tissue and bone within said patient.

* * * * *